US008015888B2

(12) United States Patent
Gross

(10) Patent No.: US 8,015,888 B2
(45) Date of Patent: Sep. 13, 2011

(54) THIN-FILM SAMPLE HOLDER

(75) Inventor: Karl J. Gross, Fremont, CA (US)

(73) Assignee: Hy-Energy, LLC, Newark, CA (US)

( * ) Notice: Subject to any disclaimer, the term of this patent is extended or adjusted under 35 U.S.C. 154(b) by 530 days.

(21) Appl. No.: 12/132,573

(22) Filed: Jun. 3, 2008

(65) Prior Publication Data
US 2008/0307905 A1 Dec. 18, 2008

Related U.S. Application Data

(60) Provisional application No. 60/944,290, filed on Jun. 15, 2007.

(51) Int. Cl.
*G01N 15/00* (2006.01)
(52) U.S. Cl. ...................................... 73/865.5
(58) Field of Classification Search ............. 73/865.5; 422/69
See application file for complete search history.

(56) References Cited

U.S. PATENT DOCUMENTS

| 3,379,303 A | 4/1968 | Jenkins | 206/570 |
| 5,360,743 A | 11/1994 | Lowell | 436/5 |
| 5,918,289 A * | 6/1999 | Scheppers et al. | 73/863.21 |
| 6,387,704 B1 | 5/2002 | Thomas | 436/55 |

OTHER PUBLICATIONS

EP Search Report, EP App. No. 08157821, dated Feb. 8, 2010.

* cited by examiner

*Primary Examiner* — Hezron Williams
*Assistant Examiner* — Tamiko D Bellamy
(74) *Attorney, Agent, or Firm* — Patterson & Sheridan, LLP

(57) ABSTRACT

A gas sorption sample chamber contains a plurality of thin-film substrates and fluidly couple said substrates to a Sieverts' device or other gas sorption analyzer. The thin-film substrates are held in proximity to each other in the sample chamber in a columnar arrangement, either in a stacked or slightly spaced configuration, to reduce free-gas volume in the sample chamber, thereby improving sorption test accuracy. The interior geometry of the chamber is configured to provide a minimal clearance between the thin-film substrates and the internal surfaces of the chamber, so that essentially all of the chamber volume is occupied by thin-film sample material and inactive substrate material. To facilitate use in a glove box, the chamber may be configured with a removable sample cartridge in which thin-film substrates are placed so that all substrates may be loaded and unloaded as a group.

20 Claims, 7 Drawing Sheets

# THIN-FILM SAMPLE HOLDER

CROSS-REFERENCE TO RELATED APPLICATIONS

The current application claims the priority benefit of the U.S. Provisional Patent Application titled, "THIN FILM SAMPLE HOLDER FOR GAS SORPTION ANALYSIS," filed on Jun. 15, 2007 and having Ser. No. 60/944,290. The subject matter of this related application is hereby incorporated herein by reference.

BACKGROUND OF THE INVENTION

1. Field of the Invention

Embodiments of the present invention relate generally to gas sorption testing, and particularly to a thin-film sample holder for gas sorption measurements.

2. Description of the Related Art

In the field of nanotechnology, it is understood that a given material can behave in a significantly different manner when arranged differently on the nanoscale, that is, on the level of individual atoms or clusters of atoms. For example, the chemistry of a given material can be altered by inducing a particular mechano-chemical strain in the material on the nanoscale during formation. In this way, with an appropriate nanoscale configuration, ordinarily inert materials have been shown to posses catalytic properties, and seemingly constant thermodynamic properties of a material, such as the enthalpy of formation of a metal with hydrogen, can be altered and even optimized for a particular application.

Thin-film deposition processes are well-suited for forming large numbers of materials that each can be organized differently on the nanoscale, such as nanotubes, etc. or in very thin layers with nanometer dimensions. Accurate measurement of the gas sorption properties of thin films, i.e., absorption, adsorption, desorption, chemisorption and physisorption, is problematic, however, since sorption testing apparatus known in the art are designed for sorption testing of bulk powders rather than thin films. When measuring the sorption properties of a bulk powder, a relatively large quantity of gas sorbing sample material is used relative to the free-gas volume of the test gas present in the sample chamber. In this way, a measurable pressure change in the sample chamber takes place during sorption testing, even at elevated pressures. For example, the PCTPro-2000, available from Hy-Energy LLC, Newark, Calif., is configured to perform sorption testing on a material sample with a sample chamber having a free-gas volume of approximately 0.5 ml after the placement of a material sample having a mass of approximately 10 to 1000 milligrams in the chamber. Relative to such bulk material samples, the mass of a thin-film material deposited on a substrate that can be tested in a conventional sorption tester sample chamber can be smaller, having, for example, up to one or more orders of magnitude less mass than a typical bulk sample. In addition, because of the geometry of a thin-film on a substrate, when placed in a conventional sorption tester sample chamber the substrate generally occupies a very small portion of the chamber volume, leaving a high free-gas volume. Thus, because the ratio of sample chamber free-gas volume to sample material mass is so high when testing a thin-film sample on a substrate, the pressure drop produced by gas sorption of the thin film is not accurately measurable using conventional pressure measuring devices.

To test a greater amount of thin-film sample material, the thin film can be removed from underlying substrates and tested as a bulk material. Such an approach allows larger masses of material to be tested while reducing the free-gas volume in the sample chamber. But because the process of mechanically removing a thin film from a substrate is likely to significantly alter the nanoscale properties of the thin-film sample material, and therefore the gas sorption behavior of the sample material, in-situ testing of a thin film as deposited on a substrate (the film and substrate together being referred to herein as a thin-film substrate) is a more rigorous and reliable approach.

Alternatively, a larger mass of thin-film sample material can be sorption tested by configuring a sample chamber to contain an entire full-sized thin-film substrate, such as a 6 inch diameter silicon wafer. FIG. 1 illustrates a wafer-sized sample chamber 100 configured for attachment to a conventional sorption testing apparatus. Wafer-sized sample chamber 100 is a "clamshell" design, configured to contain an entire substrate 103. Substrate 103 is a standard thin-film substrate, such as a 6 inch or 8 inch silicon wafer. Substrate 103 has a thin film 107 deposited thereon, where thin film 107 includes a gas-sorbing material to be tested in wafer-sized sample chamber 100. Substrate 103 is positioned on a substrate support (not shown) in wafer-sized sample chamber 100 between lid 101 and base 102, and test port 110 is fluidly coupled to a sorption-testing apparatus using a leak-resistant means known in the art. A clamping mechanism (not shown) exerts closing force 106 so that lid 101 and base 102 press against sealing member 105 with sufficient force to allow pressurization of wafer-sized sample chamber 100 during sorption testing of thin film 107.

Prior to sorption testing, material samples are typically isolated from atmospheric moisture and other contaminants by being handled in a controlled environment, such as an argon-purged glove box or other isolation chamber. Because wafer-sized chamber 100 is configured for testing a full-sized substrate (i.e., substrate 103), and because wafer-sized chamber 100 has a simple two-piece clamshell configuration, the design of wafer-sized chamber 100 facilitates the loading of a test substrate therein while contained in a glove box. The use of substrate 103 also allows for a greater mass of sample material to be tested than can be deposited on a substrate small enough for use in a conventional sorption testing chamber.

However, wafer-sized chamber 100 is not suited for performing sorption testing since such tests are commonly performed at high pressures, e.g., tens to hundred's of atmospheres. First, closing force 106 needed when wafer-sized chamber 100 is pressurized to 100 atmospheres or more is prohibitively large, requiring an impracticably large and bulky apparatus. Second, the free-gas region 104 of wafer-sized chamber 100 is too large to allow accurate sorption measurements. Although a higher mass of thin film 107 can be sorption tested in wafer-sized chamber 100 than in a standard-sized sorption sample chamber, the ratio of free-gas volume to sample material mass is still too high for an accurately measurable pressure drop to take place during most sorption tests—particularly higher pressure tests. Lastly, the potential for leakage from free-gas region 104 past sealing member 105 is too high for reliable sorption measurements. This is because wafer-sized chamber 100 has a relatively large sealing surface, i.e., sealing member 105, and any leakage out of wafer-sized chamber 100 during a sorption test directly affects the accuracy of the test. Further, the leakage rate across sealing member 105 increases as the pressure inside wafer-sized chamber 100 increase, and decreases the more that a compression force is exerted on sealing member 105. The compression force is equal to the amount by which closing force 106 exceeds the minimum force necessary to hold lid 101 and base 102 together. Thus, at higher pressure sorption tests, there is more impetus for leakage across sealing member 105 at the same time that the compression force on sealing member 105 is reduced.

Accordingly, there is a need in the art for a sorption sample chamber that can accurately perform gas sorption measurements on thin-film samples at high pressures, and facilitates loading and unloading of thin-film samples while contained in a glove box or other isolation chamber.

SUMMARY OF THE INVENTION

Embodiments of the invention contemplate a gas sorption sample chamber configured to contain a plurality of thin-film substrates and fluidly couple said substrates to a Sieverts' device or other gas sorption analyzer.

According to one embodiment, a gas sorption sample chamber comprises a pressure vessel for containing a plurality of thin-film substrates stacked in a columnar arrangement and a re-sealable fitting for fluidly coupling the pressure vessel to a gas sorption analyzer and sealing an opening in the pressure vessel that is configured for loading the thin-film substrates into the pressure vessel.

According to another embodiment, a gas sorption sample chamber comprises a thin-film sample holder having an outer surface and an internal surface that is configured to contain a plurality of thin-film substrates stacked in a columnar arrangement and maintain a first clearance around the perimeter of thin-film substrates disposed therein, a pressure vessel having the thin-film sample holder such that a second clearance maintained between an internal surface of the pressure vessel and the outer surface of the thin-film sample holder is no greater than about 1% of the internal width of the pressure vessel, and a re-sealable fitting for fluidly coupling the pressure vessel to a gas sorption analyzer and sealing an opening in the pressure vessel configured for loading the thin-film sample holder into the pressure vessel.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

Embodiments of the invention contemplate a gas sorption sample chamber configured to contain a plurality of thin-film substrates and fluidly couple said substrates to a Sieverts' device or other gas sorption analyzer. The thin-film substrates are held in proximity to each other in the sample chamber in a columnar arrangement, either stacked in direct contact or in a slightly spaced configuration, to reduce free-gas volume in the sample chamber, thereby improving sorption test accuracy. To further reduce chamber free-gas volume, the interior geometry of the chamber is configured to provide a minimal clearance between the thin-film substrates and the internal surfaces of the chamber, so that essentially all of the chamber volume is occupied by the thin-film sample holder, thin-film sample material and inactive substrate material. To minimize the potential for leakage during testing, the sample chamber is provided with an opening for loading and unloading the thin-film samples having a relatively small sealing area. For ease of use in a glove box, the chamber may be configured with a removable sample cartridge in which thin-film substrates are placed so that all substrates may be loaded and unloaded as a group.

Figure 1:
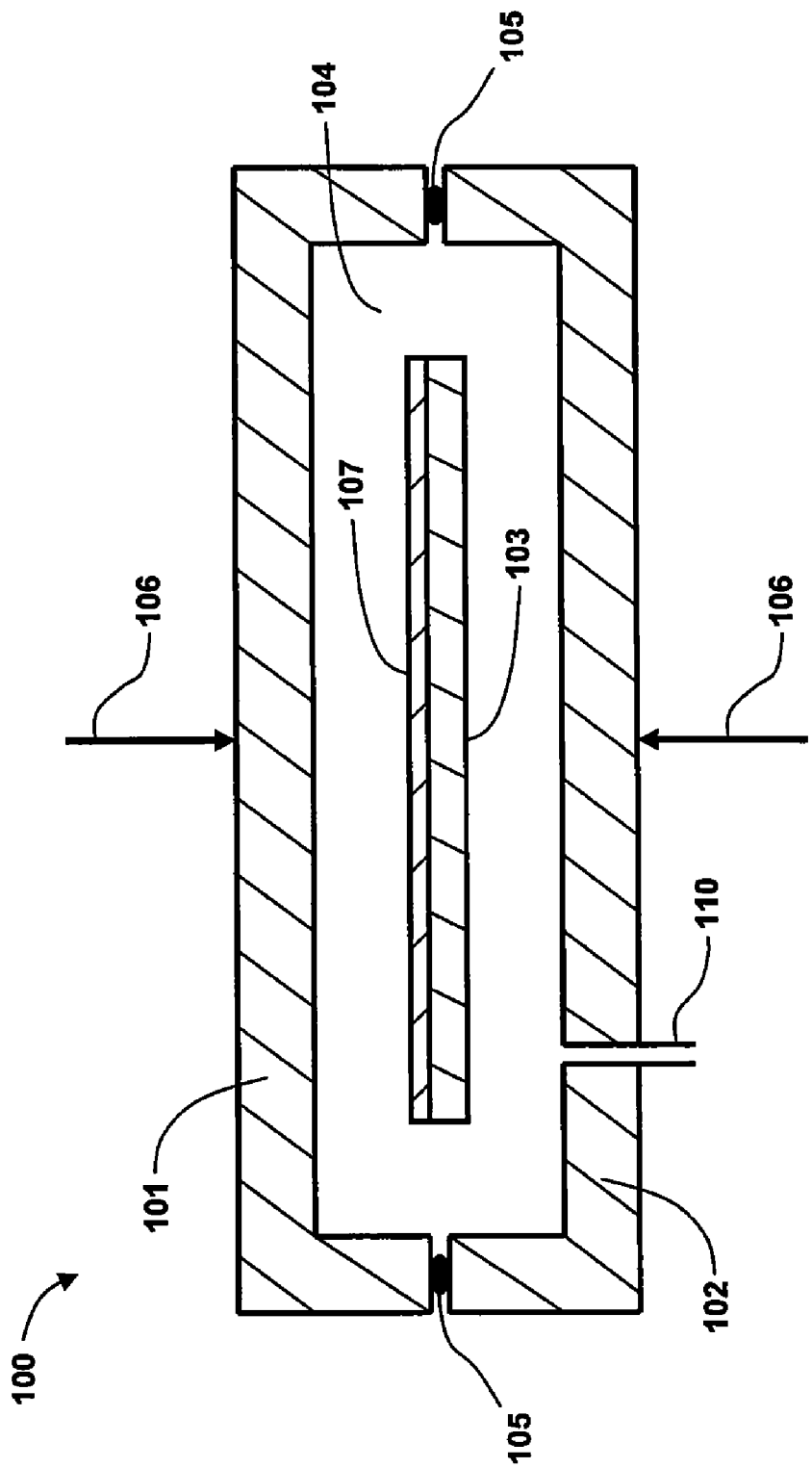
FIG. 1 illustrates a wafer-sized sample chamber configured for attachment to a conventional sorption testing apparatus.
Figure 2:
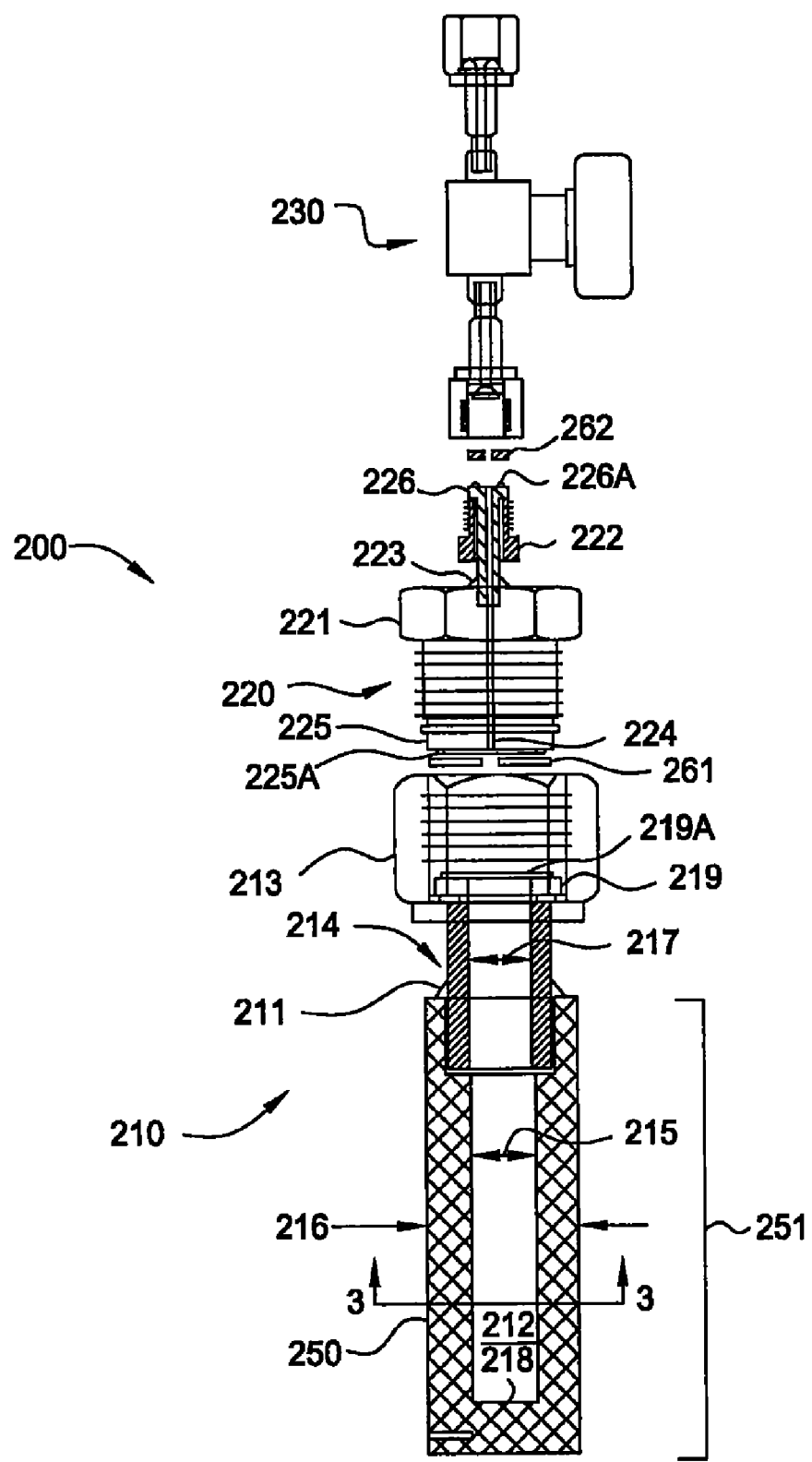
FIG. 2 illustrates an exploded schematic side view of a thin-film sample chamber, according to an embodiment of the invention.

FIG. 2 illustrates an exploded schematic side view of a thin-film sample chamber 200, according to an embodiment of the invention. Thin-film sample chamber 200 includes a pressure vessel 210, a reducer fitting 220, and an isolation valve 230. For clarity, portions of pressure vessel 210 and reducer fitting 220 are cross-sectioned in FIG. 2. Pressure vessel 210 has a wall 250, an internal volume 212, an internal diameter 215, an external diameter 216, an opening 214 located on one end of pressure vessel 210, and a threaded fitting 213 mechanically coupled to opening 214 by an airtight connection, such as a welded connection 211. Threaded fitting 213 has an inner diameter 217 that is substantially equal to internal diameter 215, so that internal volume 212 is essentially a cylindrical volume extending from a bottom surface 218 of pressure vessel 210 to the plane defined by the sealing surface 219A of gland 219. In one embodiment, threaded fitting 213 is a standard 1" VCR® fitting and inner diameter 217 and internal diameter 215 are both 0.75". In another embodiment, the internal cross-section of pressure vessel 210 is square or rectangular.

Reducer fitting 220 includes threaded fitting 221 adapted to mate with threaded fitting 213, a reduced diameter fitting 222 mechanically coupled to threaded fitting 221 by an airtight connection, such as a welded connection 223, and a small diameter conduit 224 that passes through threaded fitting 221 and reduced diameter fitting 222 as shown to fluidly couple internal volume 212 to isolation valve 230. A gland 225 with a sealing surface 225A is positioned on the end of threaded fitting 221 and another gland 226 with a sealing surface 226A is positioned on the end of reduced diameter fitting 222. Small diameter conduit 224 is configured to have the smallest internal diameter as practicable in order to reduce free-gas volume of thin-film sample chamber 200 when loaded with thin-film samples for sorption testing. In one embodiment, small diameter conduit 224 is a drilled hole passing through a modified ¼" VCR® fitting 222 and threaded fitting 221 having an inner diameter of approximately 0.05". Isolation valve 230 fluidly couples and decouples thin-film sample chamber 200 from a Sieverts' device or other gas sorption analyzer (not shown), such as a PCTPro-2000, available from Hy-Energy LLC, Newark, Calif. Isolation valve 230 is a manual or automated shut-off valve, such as a diaphragm valve, and is configured for leak-free sealing in high-pressure applications.

To ensure leak-free sealing between the subassemblies of thin-film sample chamber 200, i.e., between isolation valve 230 and reducer fitting 220, and between reducer fitting 220 and pressure vessel 210, metal face-seal gaskets 261, 262 commonly known in the art are used, such as those used with VCR® fittings and UJR® fittings, among others. Metal face-seal gaskets are particularly useful for high-pressure, vacuum, and high-temperature applications, such as sorption testing. To create a leak-tight seal, a metal gasket, e.g., metal face-seal gasket 261, is placed between the glands of two adjacent fittings, e.g., threaded fitting 213 and threaded fitting 221, the mating threaded fasteners of the fittings are tightened, and the sealing surface of each gland, e.g., sealing surface 219A and sealing surface 225A, is pressed against metal face-seal gasket 261 to form a metal-to-metal, low-leakage connection. In one embodiment, the sealing surfaces pressed against the metal gasket include one or more concentric knife-edge seals rather than a VCR®-style gland, and the metal gasket may be a relatively soft metal, such as copper, aluminum, or tin, among others. In this embodiment, instead of a VCR®-style male-female nut arrangement, as illustrated in FIG. 2, each subassembly of thin-film sample chamber 200 may be configured with a flanged connection that is compressed by multiple threaded fasteners, to uniformly press the knife-edge seals into the metal gasket.

As noted above, it is contemplated that pressure vessel 210 may be configured with different cross-sectional geometries, depending on the shape of the thin-film substrates to be tested. In one embodiment, thin-film samples for testing in thin-film sample chamber 200 are circular silicon substrates, and are stacked together in internal volume 212 to minimize free-gas volume in thin-film sample chamber 200 during sorption testing. The substrates may be stacked face-to-face or face-to-tail. In this embodiment, the plurality of circular thin-film samples to be tested may be deposited with a thin-film material simultaneously in a batch process to minimize variation of the thin-film material properties between substrates. To further reduce free-gas volume in thin-film sample chamber 200 when loaded with samples for sorption testing, the outer diameter of the thin-film substrates is only slightly less than internal diameter 215 of pressure vessel 210, as depicted in FIG. 3A.

Figure 3B:
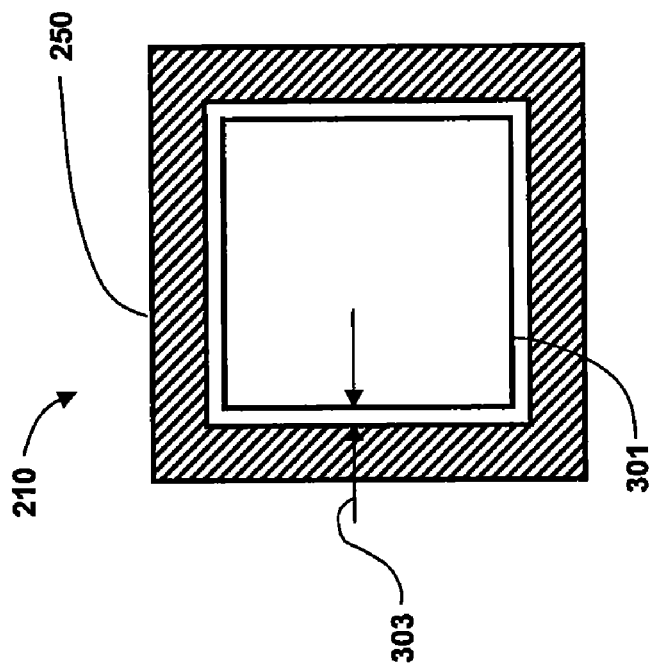
FIG. 3B illustrates a schematic cross-sectional view of a pressure vessel with a square substrate positioned therein, according to an embodiment of the invention.
Figure 3A:
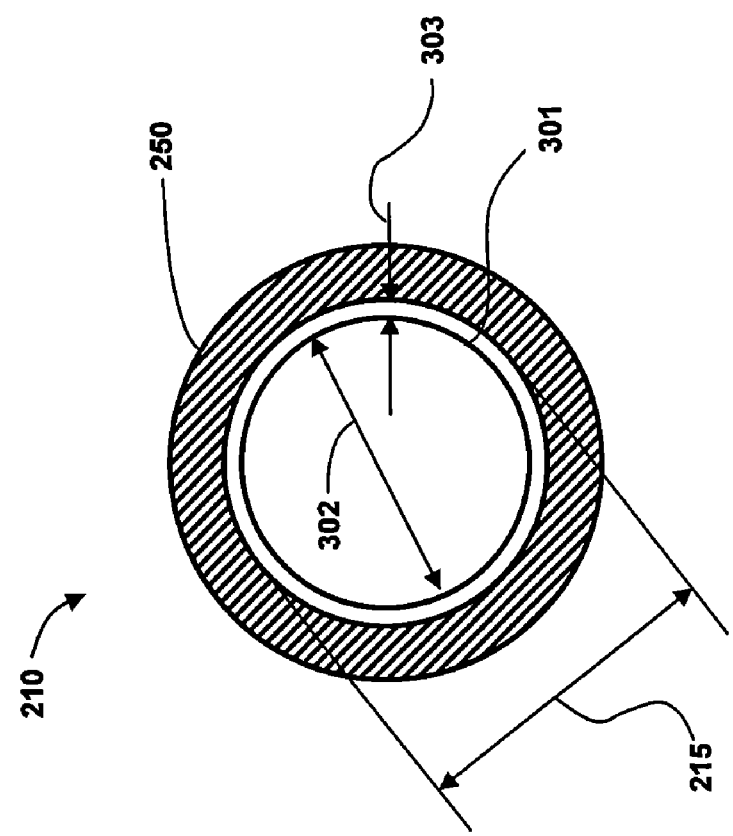
FIG. 3A illustrates a schematic cross-sectional view of a pressure vessel with a circular substrate positioned therein, according to an embodiment of the invention.

FIG. 3A illustrates a schematic cross-sectional view of pressure vessel 210 taken at section line 3-3 in FIG. 2 with a circular substrate 301 positioned therein, according to an embodiment of the invention. Because the outer diameter 302 of substrate 301 is only slightly less than internal diameter 215 of pressure vessel 210, a clearance 303 is present between the perimeter of substrate 301 and the internal surface of wall 250 of pressure vessel 210. Substrate 301 and pressure vessel 210 may be configured to minimize clearance 303, thereby greatly reducing the free-gas volume present in pressure vessel 210 during sorption testing. Clearance 303 is preferably no more than about 10% of internal diameter 215 and the free-gas volume of thin-film sample chamber 200 when loaded with a plurality of thin-film substrates is no greater than about 20% of the free-gas volume of the chamber when thin-film sample chamber 200 is not loaded thin-film substrates. In one embodiment, threaded fitting 213 and gland 219 are modified 1" VCR®-compatible fittings, internal diameter 215 is 0.75" and clearance 303 is no more than about 0.0375", and the free-gas volume of pressure vessel 210 when loaded with a plurality of substrates is less than about 7 ml. In this embodiment, pressure vessel 210 may be a tube constructed from stainless steel or other durable material not subject to outgassing and capable of undergoing the temperature and pressure changes that occur across the range of sorption tests that are typically performed on thin-film materials. Bottom surface 218 may be formed with a plate welded to the end opposite opening 214 or pressure vessel 210 may be machined from a single piece of material. One skilled in the art can readily devise other manufacturing methods for pressure vessel 210 as described herein.

In another embodiment, thin-film samples for testing in thin-film sample chamber 200 are square or rectangular, and the cross-section of pressure vessel 210 is configured accordingly, as depicted in FIG. 3B. FIG. 3B illustrates a schematic cross-sectional view of pressure vessel 210 taken at section line 3-3 in FIG. 2 with a square substrate 311 positioned therein, according to an embodiment of the invention. In this embodiment, the plurality of square thin-film samples to be tested may be diced from a single conventional substrate, such as a 6" silicon wafer. In this way, variation of the thin-film material properties between each square substrate is minimized. As described above in conjunction with FIG. 3A, substrate 311 and wall 250 of pressure vessel 210 may be configured to minimize clearance 303 therebetween. One skilled in the art will appreciate that thin-film substrates of other shapes, e.g., triangular, hexagonal, etc., can also be accommodated by a configuration of pressure vessel 210 having an appropriately shaped cross-sectional profile.

In operation, thin-film sample chamber 200 (see FIG. 2) is loaded with a plurality of thin-film substrates by separating pressure vessel 210 from reducer fitting 220, reducer fitting 220 being fluidly coupled to a gas sorption analyzer via isolation valve 230. Thin-film substrates are loaded into internal volume 212 via opening 214. As noted above, the substrates are loaded in a stacked configuration to minimize free-gas volume contained in pressure vessel 210 during sorption testing. Enough substrates are loaded into internal volume 212 to fill internal volume 212 from bottom surface 218 to sealing surface 219A of gland 219. Alternatively, excess space in internal volume 212 may be filled with other suitably sized and shaped non-absorbing materials in addition to the substrates. Thus internal volume 212 is filled with thin-film sample material and inactive substrate material, i.e., silicon, and contains virtually no free-gas volume, thereby maximizing the accuracy of sorption tests performed on the thin-film sample material. A metal gasket is positioned on sealing surface 219A and pressure vessel 210 is reassembled with reducer fitting 220. Because assembly and disassembly of thin-film sample chamber 200 only involves threading together threaded fitting 213 with threaded fitting 221, this operation can be readily performed in a glove box or other isolation chamber.

One advantage of thin-film sample chamber 200 is that the length of the sealing surfaces between each subassembly, i.e., sealing surface 219A, sealing surface 221A, etc., is relatively small compared to the sample chamber volume, and therefore the mass of thin-film sample material. This is because the length of each sealing surface of thin-film sample chamber 200 is disposed on a feature of thin-film sample chamber 200 having a relatively small dimension compared to the sample chamber volume. For example, sealing surface 219A is determined by the circumference of threaded fitting 213. The sealing surfaces of thin-film sample chamber 200 are not disposed on features thereof having relatively large dimensions compared to the sample chamber volume, such as length 251, or the perimeter of pressure vessel 210.

The low-length sealing surfaces of thin-film sample chamber 200 reduce the likelihood of unwanted leakage into or out of pressure vessel 210, thereby improving accuracy of sorption testing. In addition, the compact construction of thin-film sample chamber 200 provides enough rigidity to withstand the high forces that result from the high pressures and thermal cycling that are associated with sorption testing. This prevents thin-film sample chamber 200 from being subject to significant deflection of its components during thermal and pressure cycling, which can ordinarily produce problematic changes in the sample chamber, including leaking or failure.

Another advantage of thin-film sample chamber 200 is that the geometry of pressure vessel 210 can be optimized for a particular application. As described above, pressure vessel 210 can be designed to accommodate any shape of thin-film substrate that is required. In addition, to ensure that the pressure drop that takes place in thin-film sample chamber 200 during sorption testing can be accurately measured, other aspects of the geometry of pressure vessel 210 can be altered. For example, length 251 of pressure vessel 210 can be extended to increase the total number of thin-film substrates, and therefore mass of thin-film sample material, that can be contained therein. In this way, the pressure drop that occurs during sorption testing of the thin-film samples can be amplified to a level at least about five times greater than the resolution of a typical pressure transducer used for sorption testing, thereby ensuring an accurate assessment of the sorption capabilities of the thin-film sample material. Alternatively, clearance 303, as shown in FIGS. 3A and 3B, can be reduced to a degree that substantially eliminates the free-gas volume of thin-film sample chamber 200. Similarly, in order to optimize the mass of thin-film sample material relative to the free-gas volume associated with clearance 303, pressure vessel 210 can be configured to contain thin-film substrates having larger or smaller surface area than those already described herein.

Figure 4:
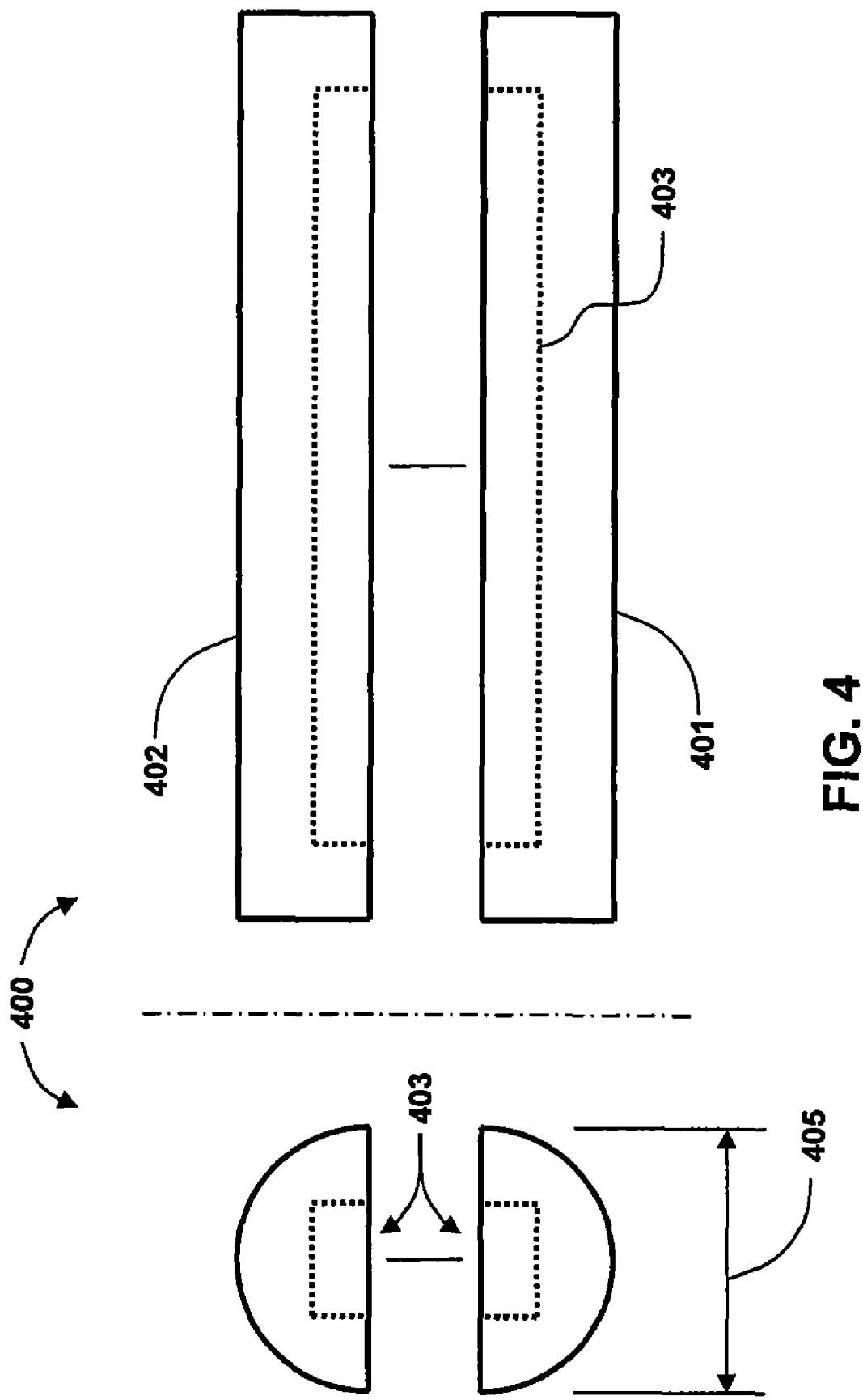
FIG. 4 illustrates schematic side and end views of a side-loading sample holder, according to an embodiment of the invention.

In one embodiment, a thin-film sample chamber includes a side-loading thin-film sample holder to facilitate loading and unloading of the chamber while in a glove box or other isolation chamber. FIG. 4 illustrates exploded side and end views of a side-loading sample holder 400, according to an embodiment of the invention. Side-loading sample holder 400 includes a base 401 and a top 402, which, when mated together, form a cylinder. Base 401 and top 402 each have a cut-out region 403 that is rectangular in cross-section, as shown in the edge view of side-loading sample holder 400. When base 401 and top 402 are mated with each other, cut-out regions 403 combine to form an elongated region that is square in cross-section and which is configured to contain a plurality of square thin-film substrates that are each substantially similar to square substrate 311, described above in conjunction with FIG. 3B. Side-loading sample holder 400 may be constructed from any durable, temperature-resistant material that is not subject to outgassing at the temperatures and pressures associated with gas sorption testing. In one embodiment, side-loading sample holder 400 is constructed of stainless steel.

Figure 5:
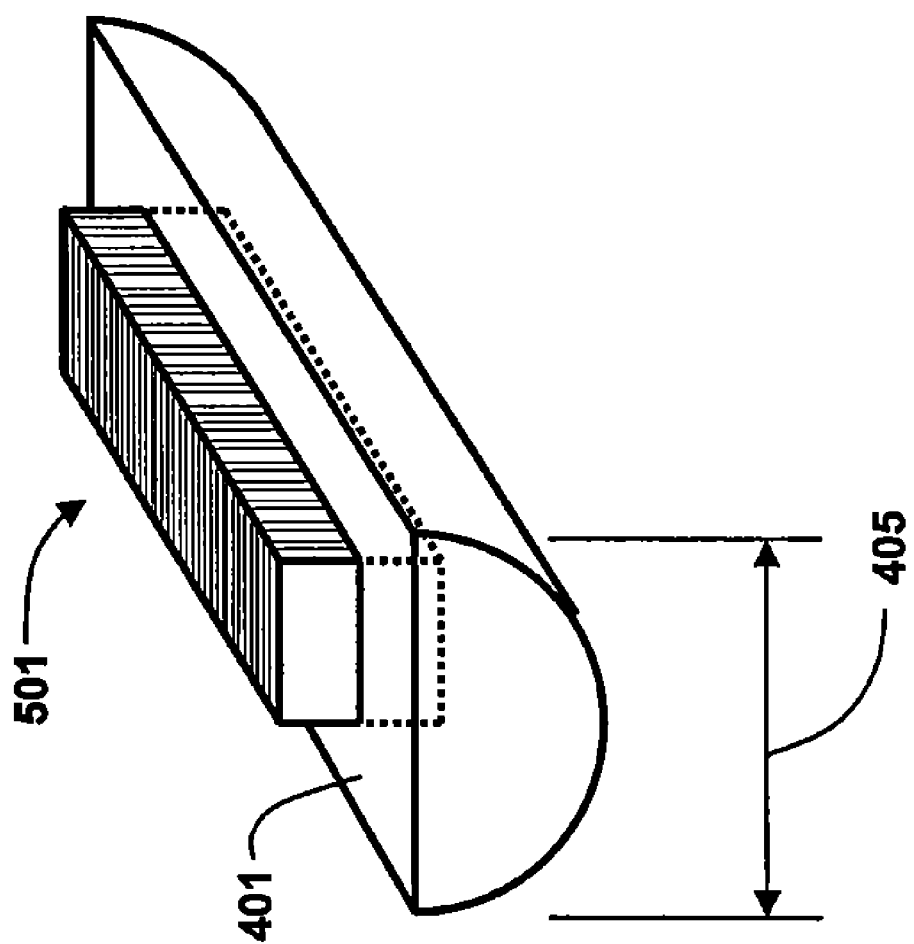
FIG. 5 illustrates a base of a side-loading sample holder after being loaded with a plurality of square thin-film substrates, according to an embodiment of the invention.

FIG. 5 illustrates base 401 of side-loading sample holder 400 after being loaded with a plurality of square thin-film substrates 501, according to an embodiment of the invention. The substrates may be stacked face-to-face or face-to-tail in a columnar arrangement. Just as the interior walls of pressure vessel 210 may be configured to maintain a very small clearance between the outer edge of the thin-film substrates contained therein, cut-out regions 403 of base 401 and top 402 may also maintain a very small clearance between the outer edges of the plurality of thin-film substrates 501 contained therein. In one embodiment, the clearance between the outer edge of the thin-film substrates and the inner surfaces of cut-out regions 403 is no more than about 10% of the width of the thin film substrates. Thus, when loaded with the plurality of thin-film substrates 501, side-loading sample holder 400 forms a substantially solid cylinder containing virtually no free-gas volume. Side-loading sample holder 400 can then be loaded into pressure vessel 210. Outer diameter 405 of side-loading sample holder 400 may be configured to fit with a tight clearance inside internal diameter 215 of pressure vessel 210, for example no greater than about 10% of internal diameter 215. In one embodiment, threaded fitting 213 is a standard 1" VCR® compatible fitting, internal diameter 215 is 0.75" and a clearance is maintained between internal diameter 215 and the outer surface of the thin-film sample holder 400 that is no more than about 0.0375". In this way, very little free-gas volume remains in pressure vessel 210 after side-loading sample holder 400 is loaded with a plurality of thin-film substrates 501 and is positioned in internal volume 212 of pressure vessel 210. In addition, the loading of square substrates into base 401 is easier and requires less dexterity than directly loading and removal of said substrates into internal volume 212 individually. Therefore, side-loading sample holder 400 facilitates the loading of a thin-film sample chamber according to embodiments of the invention while in a glove box or other isolation chamber.

One skilled in the art will appreciate that the cut-out regions 403 of side-loading sample holder 400 may be configured to accommodate thin-film substrates having other sizes and shapes as well, such as triangular, rectangular, and hexagonal, among others. Similarly, one skilled in the art will appreciate that thin-film sample holder 400 and pressure vessel 210 may be configured with a cross-sectional shape other than circular, e.g., square, rectangular, etc., and that the pressure vessel with therefore have an internal width rather than an internal diameter 215.

Figure 6A:
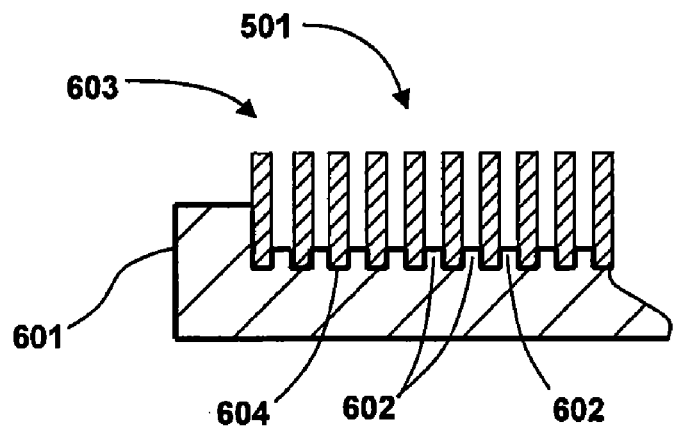
FIG. 6A illustrates a partial cross-sectional view of a base portion of a side-loading sample holder that is configured with a plurality of spacer slots on an internal surface of a cut-out region, according to an embodiment of the invention.
Figure 6B:
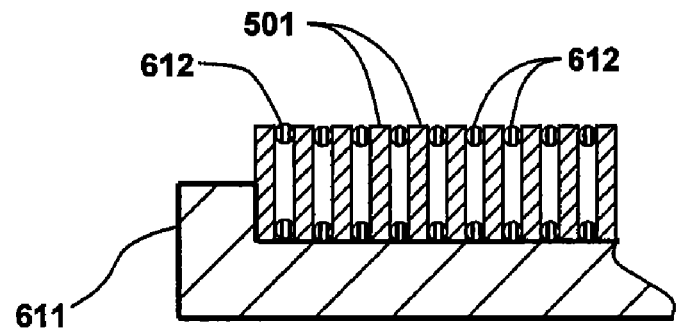
FIG. 6B illustrates a partial cross-sectional view of a base portion of a side-loading sample holder that is loaded with a combination of square thin-film substrates and spacer rings, according to an embodiment of the invention.
Figure 6C:
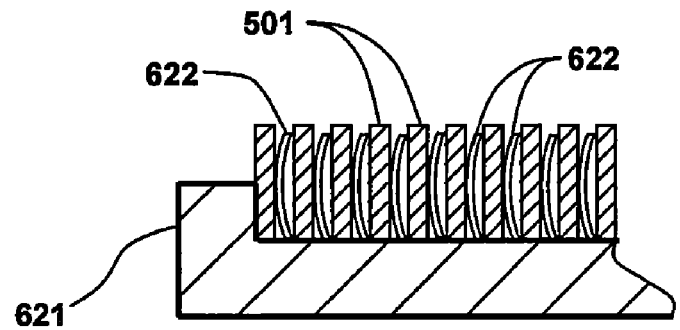
FIG. 6C illustrates a partial cross-sectional view of a base portion of a side-loading sample holder that is loaded with a combination of square thin-film substrates and curved discs, according to an embodiment of the invention.

In some applications, contact between thin-film substrates is undesirable due to the potential for damage to the thin-film sample material deposited on each substrate. It is contemplated that a side-loading sample holder, according to embodiments of the invention, may include spacing features or devices positioned between the thin-film substrates to separate the substrates from each other when loaded in the sample holder. FIG. 6A illustrates a partial cross-sectional view of a base portion 601 of a side-loading sample holder that is configured with a plurality of spacer shelves 602 on an internal surface 604 of a cut-out region 603, according to an embodiment of the invention. A plurality of square thin-film substrates 501 are loaded between spacer shelves 602 as shown, so that none of thin-film substrates 501 contact each other. In one embodiment, spacer shelves 602 are formed into internal surface 604 by a machining or other material removal process. FIG. 6B illustrates a partial cross-sectional view of a base portion 611 of a side-loading sample holder that is loaded with a combination of thin-film substrates 501 and spacer rings 612, according to an embodiment of the invention. Spacer rings 612 space thin-film substrates 501 apart so that none of said substrates contact each other. FIG. 6C illustrates a partial cross-sectional view of a base portion 621 of a side-loading sample holder that is loaded with a combination of square thin-film substrates 501 and curved discs 622, according to an embodiment of the invention. Curved discs 622 space thin-film substrates 501 apart so that none of said substrates contact each other. The use of curved discs 622 has the added benefit of only contacting each thin-film substrate 501 at two or more discrete points. In addition, one of skill in the art will appreciate that embodiments of a thin-film sample chamber that do not include a side-loading sample holder may also be loaded with spacer rings 612 or curved discs 622 to prevent significant contact between substrates loaded therein. Thin-film substrates 501 may be stacked face-to-face or face-to-tail. When stacked face-to-face, i.e., the deposited surface of each thin-film substrate 501 faces the deposited surface of an adjacent thin-film substrate 501, half as many spacing features are necessary in base portion 601 to prevent contact between the deposited surfaces of thin-film substrates 501. This is because no spacing feature is required between the undeposited surfaces of thin-film substrates 501, which are positioned to be in contact with each other when the substrates are stacked face-to-face. Further, it is understood that embodiments described in conjunction with FIGS. 6A-C may also be adapted for applications in which thin-film substrates 501 are not square in shape.

Figure 7:
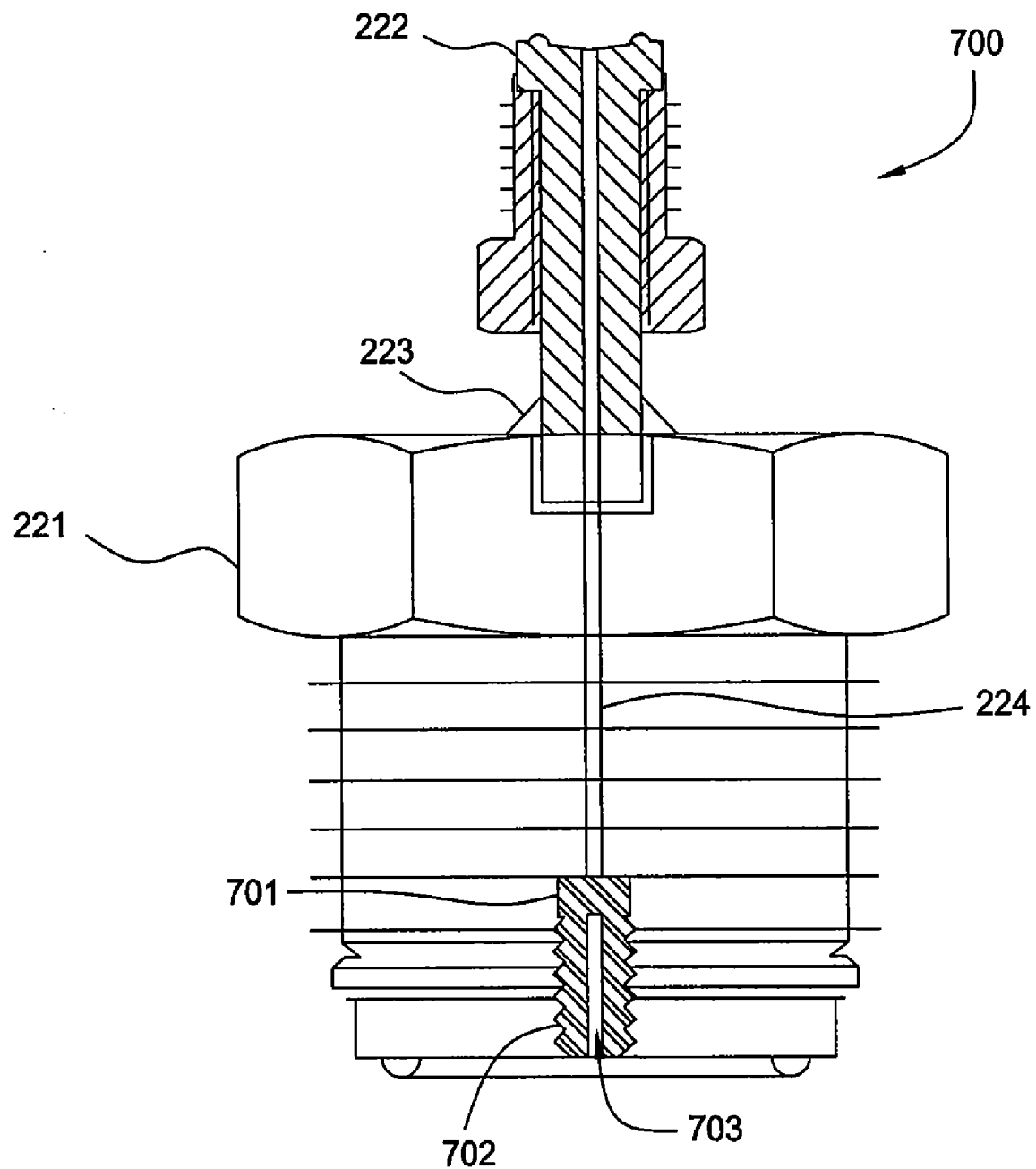
FIG. 7 illustrates a reducer fitting with an inline filter, according to an embodiment of the invention.

As noted above, leakage across sealing surfaces into or out of thin-film sample chamber 200 during sorption testing directly affects the results of the sorption test, since the pressure change caused by said leakage is assumed to have occurred due to sorption of gas into or out of the thin-film sample material. Because particle contamination of sealing surfaces is a known cause of leakage, both in sorption sample chambers and in the process plumbing of gas sorption analyzers, it is contemplated that a thin-film sample chamber, according to embodiments of the invention, may include in-line particle filters. FIG. 7 illustrates a reducer fitting 700 with an inline filter 701, according to an embodiment of the invention. Reducer fitting 700 is similar in construction to reducer fitting 224, described above in conjunction with FIG. 2. Inline filter 701 is a particle filter, such as a fritted filter, disposed in the small diameter conduit 224 passing through reducer fitting 700. In this embodiment, inline filter 701 is held in place by filter retainer screw 702 as shown, where filter retainer screw 702 is a vented screw. Vent 703 of filter retainer screw 702 may be configured with the same inner diameter as small diameter conduit 224. Inline filter 701 is configured to prevent contaminating particles from passing through small diameter conduit 224, either from the pressure vessel of a thin-film sample chamber to a gas sorption analyzer or vice-versa. The nominal pore size of inline filter 701, i.e., the minimum particle size effectively removed thereby, is application dependent, but is generally no larger than about 100 microns.

In another embodiment, the metal face-seal gaskets used to seal the subassemblies of a thin-film substrate sample chamber are configured to include an inline filter. Such gasket filters, such as sintered metal filters, are well known in the art, and can be used in place of metal face-seal gaskets 261, 262 of thin-film sample chamber 200.

While the foregoing is directed to embodiments of the present invention, other and further embodiments of the invention may be devised without departing from the basic scope thereof, and the scope thereof is determined by the claims that follow.

I claim:

1. A gas sorption sample chamber, comprising:
   a pressure vessel is configured to contain a plurality of thin-film substrates stacked in a columnar arrangement; and
   a re-sealable fitting for fluidly coupling the pressure vessel to a gas sorption analyzer and sealing an opening in the pressure vessel that is configured for loading the thin-film substrates into the pressure vessel.

2. The gas sorption sample chamber of claim 1, wherein the re-sealable fitting comprises a threaded fastener and a metal gasket.

3. The gas sorption sample chamber of claim 2, wherein the re-sealable fitting further comprises a circular gland having a sealing surface, the metal gasket comprises a metal face-seal gasket, and the threaded fastener comprises an adapter.

4. The gas sorption sample chamber of claim 2, wherein the re-sealable fitting comprises a knife-edge seal.

5. The gas sorption sample chamber of claim 1, wherein an internal surface of the pressure vessel is configured to maintain a clearance around the perimeter of the columnar arrangement of substrates and the clearance is no greater than about 10% of an internal width of the pressure vessel.

6. The gas sorption sample chamber of claim 1, wherein an internal surface of the pressure vessel is configured to maintain a clearance around the perimeter of the columnar arrangement of substrates and the free-gas volume of the chamber when the chamber is loaded with a plurality of thin-film substrates is no greater than about 20% of the free-gas volume of the chamber when the chamber is not with loaded thin-film substrates.

7. The gas sorption sample chamber of claim 1, wherein the re-sealable fitting comprises a reducer fitting having a small diameter conduit configured to fluidly couple the pressure vessel and the gas sorption analyzer.

8. The gas sorption sample chamber of claim 7, wherein the small diameter conduit has a diameter of no greater than about 0.05".

9. The gas sorption sample chamber of claim 7, wherein the reducer fitting comprises a ¼" adapter.

10. The gas sorption sample chamber of claim 1, wherein the re-sealable fitting comprises an isolation valve configured to fluidly couple and decouple the pressure vessel and the gas sorption analyzer.

11. The gas sorption sample chamber of claim 1, wherein the columnar arrangement of substrates resides within a thin-film sample holder having an internal surface configured to maintain a clearance around the perimeter of thin-film substrates disposed therein.

12. The gas sorption sample chamber of claim 11, wherein the columnar arrangement of substrates substantially fills the internal volume of the pressure vessel.

13. The gas sorption sample chamber of claim 12, wherein the columnar arrangement of substrates fills 80% of the internal volume of the pressure vessel.

14. The gas sorption sample chamber of claim 11, wherein the clearance between the internal surface of the thin-film sample holder and the perimeter of the thin-film substrates disposed therein is no greater than about 0.0375".

15. The gas sorption sample chamber of claim 11, wherein the second clearance between the internal surface of the thin-film sample holder and the perimeter of the thin-film substrates disposed therein is no greater than about 10% of the width of a thin-film substrate.

16. The gas sorption sample chamber of claim 11, wherein the thin-film sample holder comprises a base configured to support a plurality of thin-film substrates stacked in a columnar arrangement.

17. The gas sorption sample chamber of claim 16, wherein the base is configured with spacing features configured to prevent contact between each of the plurality of thin-film substrates.

18. The gas sorption sample chamber of claim 17, wherein the spacing features are selected from the group consisting of spacer shelves formed in an internal surface of the thin-film sample holder, spacer rings disposed between each of the plurality of thin-film substrates, and curved discs disposed between each of the plurality of thin-film substrates.

19. A gas sorption sample chamber, comprising:
a thin-film sample holder having an outer surface and an internal surface that is configured to contain a plurality of thin-film substrates stacked in a columnar arrangement and maintain a first clearance around the perimeter of thin-film substrates disposed therein;
a pressure vessel including the thin-film sample holder such that a second clearance maintained between an internal surface of the pressure vessel and the outer surface of the thin-film sample holder is no greater than about 10% of the internal width of the pressure vessel; and
a re-sealable fitting for fluidly coupling the pressure vessel to a gas sorption analyzer and sealing an opening in the pressure vessel configured for loading the thin-film sample holder into the pressure vessel.

20. The gas sorption sample chamber of claim 19, wherein the first clearance is not greater than about 0.0375", the second clearance is not greater than about 0.0375", and the free-gas volume of the chamber is no greater than about 7 ml when the chamber is loaded with a plurality of thin-film substrates.

* * * * *